United States Patent [19]
McCarty

[11] Patent Number: 5,439,452
[45] Date of Patent: Aug. 8, 1995

[54] LIMIT STOP VALVE INFUSION DEVICE

[75] Inventor: Read S. McCarty, Hingham, Mass.

[73] Assignee: Children's Medical Ventures, Inc., South Weymouth, Mass.

[21] Appl. No.: 188,849

[22] Filed: Jan. 31, 1994

[51] Int. Cl.[6] .................... A61M 5/00; F16K 51/00
[52] U.S. Cl. .................... 604/248; 604/183; 604/186; 137/625.22; 251/288
[58] Field of Search .............. 251/309, 288; 137/625.22; 604/30, 31, 248, 247, 246, 407, 183, 186

[56] References Cited

U.S. PATENT DOCUMENTS

| | | | |
|---|---|---|---|
| 292,824 | 2/1884 | Kennedy | 251/288 |
| 1,850,132 | 3/1932 | Morse | 604/186 |
| 2,032,723 | 3/1936 | Schweser | 604/186 |
| 2,485,842 | 10/1949 | Pennington | 604/186 |
| 4,210,173 | 7/1980 | Choksi et al. | 604/186 |
| 4,219,021 | 8/1980 | Fink | 604/248 |
| 4,253,501 | 3/1981 | Ogle | 604/246 |
| 5,002,528 | 3/1991 | Palestrant | 604/246 |
| 5,176,658 | 1/1993 | Ranford | 604/30 |

*Primary Examiner*—C. Fred Rosenbaum
*Assistant Examiner*—Mark Bockelman
*Attorney, Agent, or Firm*—J. E. Brunton

[57] ABSTRACT

A closed-system, combination infusion and flush set which enables safe administration of both medicaments and flush solutions to a patient with great accuracy using conventional large volume parenteral bags. The administration set comprises a specially designed rotatable valve member for controlling fluid flow through the set and includes a stop post which positively blocks rotation of the valve member to a position that permits the flow of flush solution toward the patient.

2 Claims, 2 Drawing Sheets

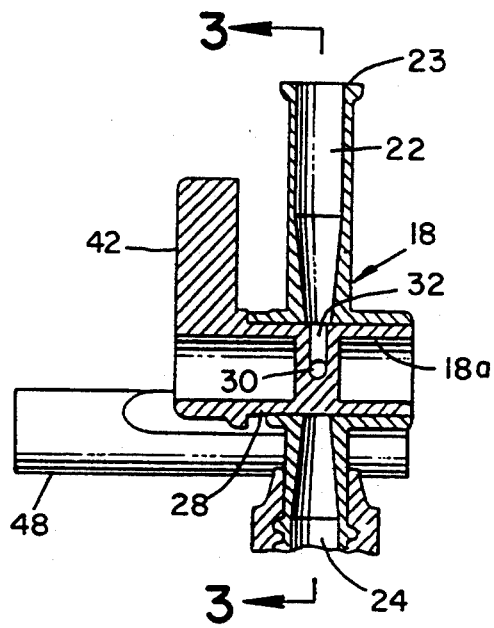
FIG. 2
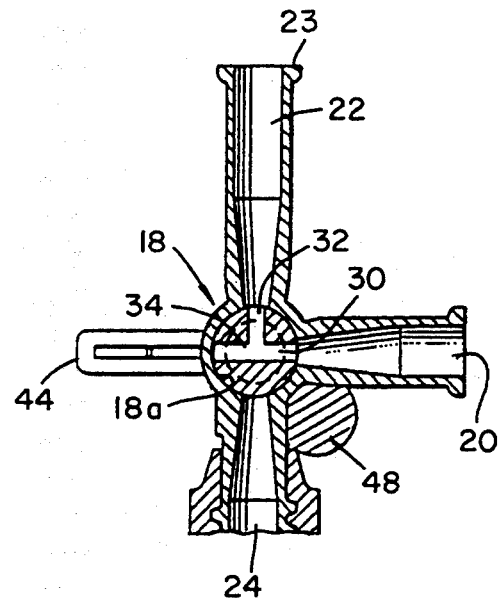
FIG. 3
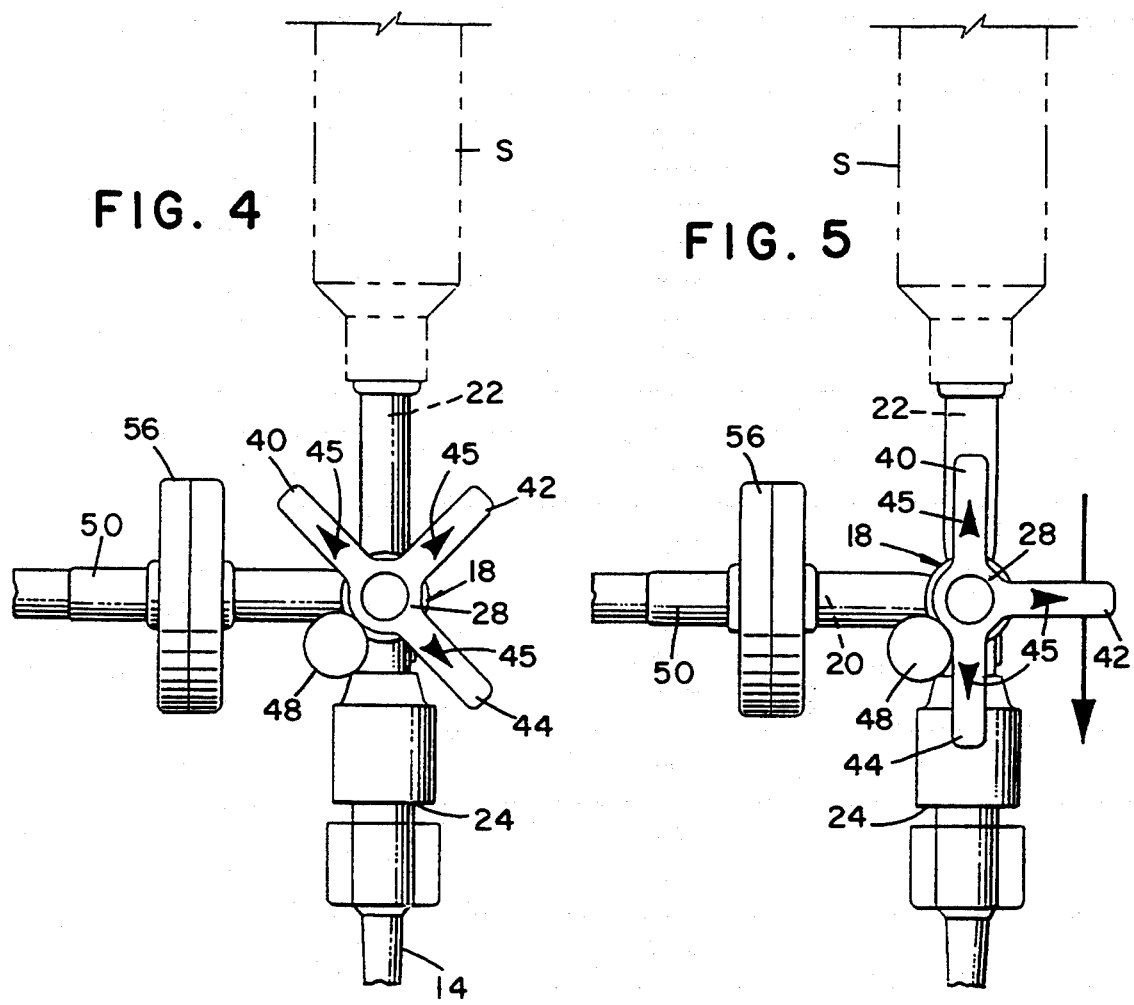
FIG. 4
FIG. 5

LIMIT STOP VALVE INFUSION DEVICE

BACKGROUND OF THE INVENTION

1. Field of the Invention

The present invention relates generally to infusion devices. More particularly, the invention concerns a novel, closed-system, combination infusion and flush set which enables safe administration of both medicaments and flush solutions with great accuracy using conventional large volume parenteral bags.

2. Discussion of the Invention

Various types of fluid administration sets have been suggested in the past for the therapeutic introduction into a patient of numerous types of fluids. For example, prior art administration sets are typically used to deliver fluids intravenously (IV sets) and usually are sterile, pyrogen-free and disposable. Although the construction of the administration sets vary somewhat from manufacturer to manufacturer, they all have certain basic components. These include a spike to pierce the rubber closure or plastic seal on the solution container, a drip chamber to trap air and permit adjustment of flow rate and a length of polyvinyl chloride tubing terminating either in a gum-rubber injection port or in a luer connector. An adjustable clamp on the tubing pinches the tubing to regulate flow. However, this approach to flow regulation and control is crude and often unreliable either because of clamp malfunction, human error, or both.

Intravenous fluids, which are sterile solutions typically of simple chemicals such as sugars, amino acids or electrolytes, are commonly used for a number of clinical conditions including correction of disturbances in electrolyte balance, correction of disturbances in body fluids (fluid replacement), and use as anti-bacterials, and vehicles for other medications and drug substances.

In the past, the intermittent administration to the patient of multiple fluids has been accomplished either through direct intravenous injection, or through the use of "piggybacking" wherein a second container is interconnected with the venipuncture site of the administration set via a "Y" site. In practicing this technique, one port of the "Y" site is connected to the tubing of the administration set, one port is connected to the second container, and the third port of the Y site is connected to the venipuncture site. When the prior art administration set is to be used in piggyback administration, the set is typically provided with a built-in check valve. When the piggyback is connected to the set and started, the check valve automatically closes off the primary infusion. When the piggyback runs out, the check valve automatically opens, thereby restarting the primary infusion.

In accordance with the prior art practices, when it is necessary to flush the system with a saline solution, or the like, the closure on the flush solution container is pierced with the spike of the administration set, the clamp is opened and the flush solution is allowed to flow by force of gravity through the delivery line. This practice must be closely monitored by competent medical personnel to insure that the flow of the flush solution toward the patient is precisely controlled. Since the uncontrolled flow of the flush solution to the patient can be potentially catastrophic, great care must be taken to prevent free flow of the flush solution toward the patient.

A recent development in the administration of medications to patients incorporates the use of a mechanical syringe pump. A pre-filled syringe is placed in an apparatus, which is programmed to depress the plunger of the syringe at a fixed rate over a fixed period of time. Use of a syringe pump is particularly useful in administration of medications over a period of time where a single bolus injection of medication cannot be tolerated by the patient. It is common practice to flush the IV line with any number of sterile flush solutions, such as saline, in order to administer the full dose of medication to the patient.

In certain patients, particularly neonates, the amount of medication is small and the residual medication in the line which must be flushed may account for a significant percentage of medication prescribed. If the syringe pump is used to slowly deliver medication over time, the use of a bolus flush to clear the residual medication in the line makes little sense as, for example, 60% of the drug may be give over 15 minutes and the remaining 40% which is the residual volume in the IV line which, with a bolus flush, may be administered in 15 seconds. In order to administer the full amount of medication slowly, the flush solution may be administered by the syringe pump. Prior to the present invention, a new syringe with the correct flush solution had to be prepared by the hospital's pharmacy, distributed to the correct patient, and placed in the syringe pump. The prior art was time consuming, costly, prone to error and raised the possibility of contaminating the patient by medical personnel inadvertently touching the connection points.

In the past, a second container containing the flush solution, may have been available at the bedside to allow medical personnel to draw up the flush solution. This required the use of needles to enter the container adding cost and the possibility of needle sticks. Also, if the flush container became contaminated due to periodic re-entering the container with a needle, the patient could become infected when the flush solution was administered.

Also, in the past, a second container containing the flush solution, could be connected to the patient administration IV Set via a four-way valve or stop cock. After the syringe in the pump was empty of its medication, medical personnel would open a fluid path from the syringe to the container of flush solution and draw up the flush solution into the syringe. The fluid path would then be opened from the syringe to the patient and the syringe pump set to slowly administer the flush solution. Such a system eliminates the need for pre-filled syringes as in the prior example. It also eliminated the need for needles to re-enter a bag of flush solution by the bedside. However, if the fluid pathway was incorrectly opened between the flush solution and the patient, an uncontrolled flow of flush solution to the patient could result with a potential catastrophic result.

The apparatus of the present invention elegantly overcomes various drawbacks of prior art administration sets by providing within the system a stop cock of unique design that positively controls the direction of flow of both IV and flush solutions to the patient. More particularly, as will become apparent from the description which follows, the novel design of the apparatus of the present invention provides a positive control, closed system which uses a syringe pump for administration of both intravenous drugs and flush solutions. With the apparatus of the invention, fluid flow can be precisely regulated and conventional large volume parenteral bags can safely be used for line flush without fear of possible free flow of the flush solution to the patient.

SUMMARY OF THE INVENTION

It is an object of the invention to provide a novel, closed-system combination infusion and flush set which enables safe administration of both medicaments and flush solutions to a patient with great accuracy using conventional large volume parenteral bags.

It is another object of the invention to provide an infusion set of the aforementioned character which includes positive means for preventing the flow of flush solution toward the patient at any time.

More particularly, it is an object of the invention to provide a novel administration set of the character described which embodies a stop cock of unique design that controls the flow of both IV and flush solutions to the patient and positively prevents the flow of flush solutions toward the patient.

Another object of the invention is to provide an administration set of the class described which eliminates bolus injection of residual line volume, minimizes touch contamination and enables administration of flush solutions with the same accuracy as administration of medications.

BRIEF DESCRIPTION OF THE DRAWINGS

FIG. 2 is a cross-sectional view taken along lines 2—2 of FIG. 1.

FIG. 3 is a cross-sectional view taken along lines 3—3 of FIG. 2.

FIG. 4 is an enlarged, fragmentary view of the stop cock portion of the apparatus showing the stop cock in a closed position.

FIG. 5 is a fragmentary view similar to FIG. 4, but showing the stop cock in a position to permit flow between the syringe port of the stop cock and the conduit leading to the venipuncture site.

DISCUSSION OF THE INVENTION

Figure 1:
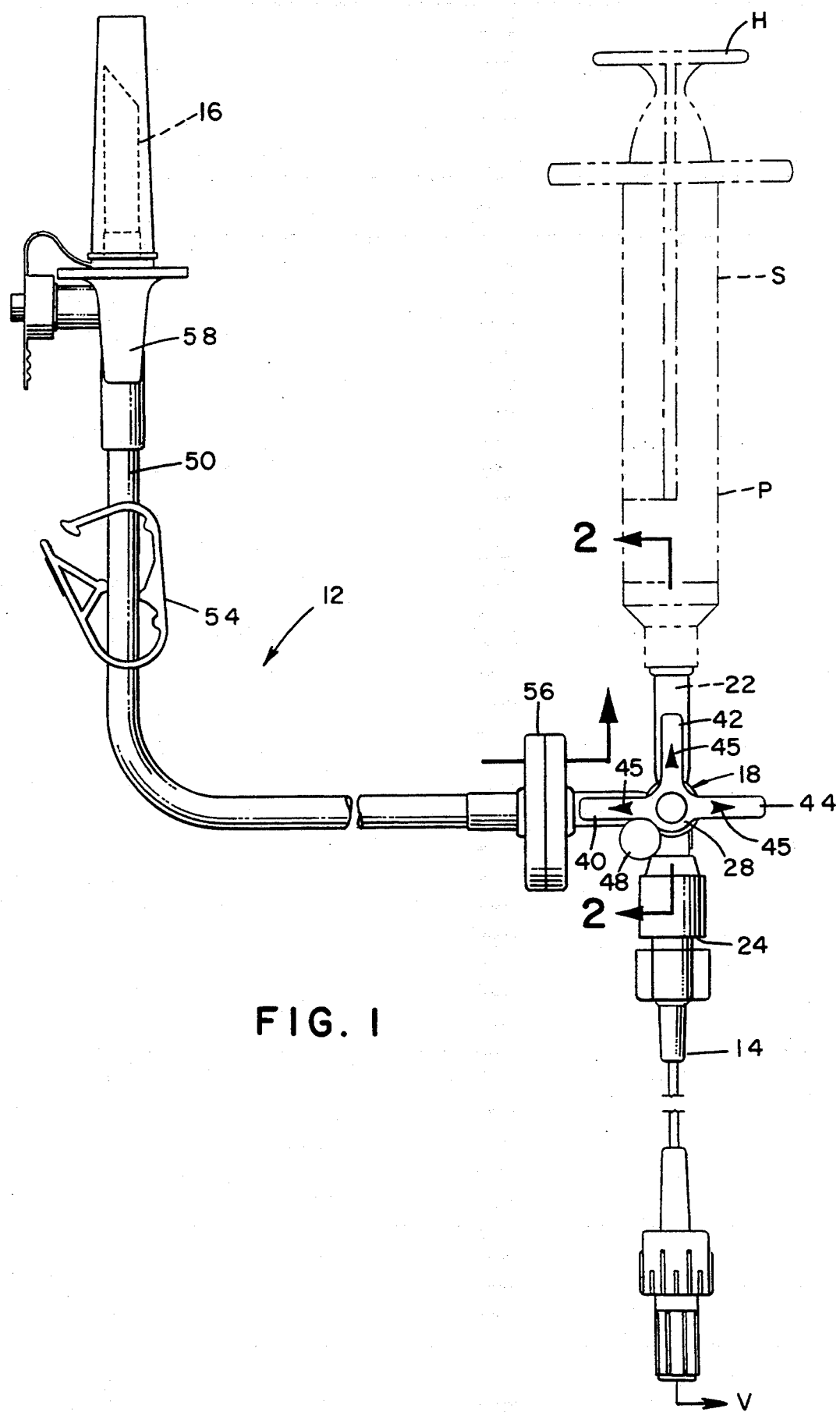
FIG. 1 is a side-elevational view of one form of the administration set of the present invention.

Referring to the drawings and particularly to FIGS. 1, 2 and 3, one form of the apparatus for controlling the flow of fluids from a solution container toward the patient is there illustrated and generally designated by the numeral 12. In this form of the invention, the apparatus comprises a first fluid conduit 14 having a fluid inlet and a fluid outlet which is interconnectable with the venipuncture site "V". To control fluid flow between the inlet spike 16 of the apparatus, which is adapted to pierce the closure on the solution container, and the outlet of the first fluid conduit 14 there is provided a flow control means of unique design. As best seen by referring to FIG. 3, the flow control means here comprises a valve body 18 having an internal chamber 18a, first and second fluid inlets 20 and 22 and a fluid outlet 24 to which first fluid conduit 14 is connected. Inlet 22 is provided with connector means such as a luer connector 23 for interconnection with a syringe "S". Syringe "S" is of conventional construction having an internal plunger "P" which is movable by handle "H" from the downward position shown in FIG. 1 to an upward or retracted pumping position. The syringe includes means for Its interconnection with the connector means. For certain applications, the connector means can comprise a septal port for penetration by a syringe cannula.

Disposed within chamber 18a of the valve body 18 is valve means for controlling fluid flow into first fluid inlet 20 and for selectively controlling fluid flow between first fluid inlet 20 and second fluid inlet 22 and between second fluid inlet 22 and fluid outlet 24. As best seen by referring to FIGS. 2 and 3, the valve means of the present form of the invention, comprises a valve member 28 which is rotatably mounted within valve body 18. Valve member 28 has first, second and third circumferentially spaced, interconnected fluid flow passageways 30, 32, and 34 respectively. As indicated in FIGS. 1, 4, and 5, valve member 28 is rotatable from a first position shown in FIG. 1 to a second, valve closed position shown in FIG. 4, and from the closed position to a third position shown in FIG. 5. When the valve member is in the first position shown in FIG. 1, fluid can flow between the first and second fluid inlets 20 and 22 of the valve body via first and second flow passageways 30 and 32. When the valve member is in the second position shown in FIG. 4, fluid flow through each passageway 30, 32, and 34 is blocked and the valve is closed. When the valve member is in the third position shown in FIG. 5, fluid flow is permitted between inlet 22 of the valve body 18 and outlet 24 thereof via first and third flow passageways 30 and 34 respectively.

To assist in rotating valve member 28, there are provided gripping means shown here as first, second and third circumferentially spaced, outwardly extending fingers 40, 42, and 44 respectively. Fingers 40, 42, and 44 are preferably integral with the valve member and are provided with arrows 45 indicating the directions of fluid flow through the valve. Also forming an important feature of the flow control means of the present invention is stop means for positively preventing fluid flow between first fluid inlet 20 and fluid outlet 24. In the form of the invention shown in the drawings, the stop means comprises a stop post 48 which is integrally formed with or bonded to valve body 18. Stop post 48 is engagable by third finger 44 when the valve member is moved into the position shown in FIG. 5, wherein fluid flow between inlet 22 and outlet 24 is permitted. With this construction, further valve rotation in a clockwise direction is positively prevented so that finger 45 can never be aligned with inlet 20.

Referring to FIGS. 3 and 4, it is to be noted that when it is desired to close the valve to prevent any fluid flow therethrough, the valve member is moved into the position shown in FIG. 4. As the valve member is rotated, fluid passageways 30, 32, and 34 will rotate in a clockwise direction through an angle of approximately 45 degrees so that the ends of the passageways are in sealing engagement with the wall of internal chamber 18a body portion 18 thereby blocking fluid flow through any of the inlet or outlet ports of the flow control means.

When the valve member is in the position shown in FIG. 1, passageway 30 aligns with inlet passageway 20, and passageway 32 aligns with inlet passageway 22. With the valve in this position, retraction of the syringe plunger will cause fluid to be drawn from the solution container into the syringe chamber via spike 16 and second fluid conduit 50. However, with the valve in this position, fluid flow between the solution container and the venipuncture site is precluded.

When the valve body is rotated 90 degrees into the position shown in FIG. 5, fluid passageway 30 will move into alignment with second inlet 22 and fluid passageway 34 will move into alignment with fluid outlet 24. With the valve in this position, inward movement of the syringe plunger will cause the fluid contained within the syringe to flow into conduit 14 and toward the venipuncture site "V". However, as previously mentioned and as indicated in FIG. 5, the stop means or stop post 48 prevents and further clockwise rotation of the valve means and positively precludes fluid flow between inlet passageway 20 and outlet passageway 24.

In the form of the invention shown in FIG. 1, the administration set also includes a closure clamp assembly 54 of conventional construction (FIG. 1) for blocking fluid flow through conduit 50. Also provided is a check valve 56 which is of standard construction and is readily commercially available. Interconnected with spike 16 is a conventional drip chamber 58.

In normal use of the apparatus of the invention, the valve is moved into the closed position shown in FIG. 4. Next, line clamp 54 is closed and the container containing the flush solution is interconnected with the system using spike 16. With the flush solution container connected to spike 16, syringe "S" containing the desired medication to be infused to the patient is then attached to inlet port 22 of the stop cock. Next, the valve member of the stop cock is turned from the closed position shown in FIG. 4 to the position shown in FIG. 5 wherein a fluid flow path is opened between inlet port 22 and outlet port 24 of the stop cock. With the valve in this syringe-to-patient position, the medication can be delivered to the patient by depressing the plunger "P" of the syringe.

Following the infusion of the medication, the stop cock is rotated in a counterclockwise direction to the position shown in FIG. 1 wherein fluid can flow between the flush solution container and inlet 20 of the stop cock. With the stop cock in this position, plunger "P" of syringe "S" is retracted to fill the syringe with the desired volume of flush solution. Once the syringe is filled, flush line clamp 54 is closed and the stop cock is turned clockwise to return to the position shown in FIG. 5. With the stop cock in this position, the syringe plunger is once again forced inwardly causing the flush solution to flow from the syringe "S" through inlet port 22 and outlet port 24. After completion of the flush step, the stop cock is rotated counterclockwise to returned to the closed position shown in FIG. 4. As previously mentioned, stop post 48 at all times prevents accidental opening of the stop cock to a position where flush solution can flow to the patient.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. An apparatus for controlling the flow of fluids from a fluid container toward a patient, comprising:
 (a) a first fluid conduit having an inlet and an outlet, said outlet being interconnectable with the patient;
 (b) flow control means for controlling fluid flow between the fluid container and said outlet of said first fluid conduit, said flow control means comprising:
  (i) a valve body having an internal chamber, first and second fluid inlets and a fluid outlet, said fluid outlet being connected to said inlet of said first fluid conduit said valve body also having first, second and third circumferentially spaced, outwardly extending fingers;
  (ii) valve means disposed within said valve body for controlling fluid flow into said first fluid inlet and for selectively controlling fluid flow between said first fluid inlet and said second fluid inlet and between said second fluid inlet and said fluid outlet, said valve means comprising a valve member rotatable within said internal chamber of said valve body, said valve member having first, second, and third circumferentially spaced fluid flow passageways, said valve member being rotatable between a first position permitting fluid flow between said first and second inlet of said valve body and said outlet thereof via said first and third fluid flow passageways, said third finger circumferentially aligned with said third passageway; and
  (iii) stop means for positively preventing fluid flow between said first fluid inlet and said fluid outlet, said stop means comprising and outwardly projecting stop post connected to said valve body for engagement with said third finger of said gripping means to prevent alignment thereof with said first inlet of said valve body; and
 (c) a second fluid conduit having an inlet interconnectable with the fluid container and an outlet connected to said first fluid inlet of said valve.

2. An apparatus for controlling the flow of fluids from a fluid container toward a patient, comprising:
 (a) a first fluid conduit having an inlet and an outlet, said outlet being interconnectable with the patient;
 (b) flow control means for controlling fluid flow between the fluid container and said outlet of said first fluid conduit, said flow control means comprising:
  (i) a valve body having an internal chamber, first and second fluid inlets and a fluid outlet, said fluid outlet being connected to said inlet of said first fluid conduit said valve body including first, second, and third circumferentially spaced fingers integrally formed with said valve body and being of substantially equal length;
  (ii) valve means disposed within said hollow body for controlling fluid flow into said first fluid inlet and for selectively controlling first flow between said first fluid inlet and said second fluid inlet and between said second fluid inlet and said fluid outlet said valve means comprising a valve member rotatable within said internal chamber of said valve body, said valve member having first, second and third circumferentially spaced fluid flow passageways, said valve member being rotatable between a first position permitting fluid flow between said first and second inlets of said valve body via said first and second fluid flow passageways and a second position permitting fluid flow between said second inlet of said valve body and said outlet thereof via said first and third fluid flow passageways, said third finger circumferentially aligned with said third flow passageway; and (iii) stop means for positively preventing fluid flow between said first fluid inlet and said fluid outlet, said stop means comprising an outwardly projecting stop post affixed to said valve body intermediate said first fluid inlet and said fluid outlet for engagement with said third finger of said gripping means of said valve body to prevent alignment thereof with said first inlet of said valve body; and (c) a second fluid conduit having an inlet interconnectable with the fluid container and an outlet connected to said first fluid inlet of said valve body.

* * * * *